United States Patent [19]

Seger et al.

[11] Patent Number: 5,296,112
[45] Date of Patent: Mar. 22, 1994

[54] OXYGEN MONITORING DEVICES

[75] Inventors: John L. Seger, Portland; Paul G. LaHaye, Kennebunk, both of Me.

[73] Assignee: H.P.S. Merrimac, Inc., South Portland, Me.

[21] Appl. No.: 892,211

[22] Filed: Jun. 2, 1992

[51] Int. Cl.$^5$ .............................. G01N 27/26
[52] U.S. Cl. ..................... 204/153.18; 204/424; 204/425; 204/427
[58] Field of Search ............ 204/424, 425, 427, 153.18

[56] References Cited

U.S. PATENT DOCUMENTS

| | | | |
|---|---|---|---|
| 4,505,790 | 3/1985 | Mase et al. | 204/425 |
| 4,749,466 | 6/1988 | Masson et al. | 204/427 |
| 4,875,990 | 10/1989 | Kodacki et al. | 204/428 |

OTHER PUBLICATIONS

Publication "In Situ Oxygen Analyser", a publication of Dynatron, Inc., P.O. Box 745, Wallingford, CT 06492, author(s) unknown, pp. 4–11 inclusive:publication date is unknown.

Primary Examiner—John Niebling
Assistant Examiner—Bruce F. Bell
Attorney, Agent, or Firm—William G. Rhines

[57] ABSTRACT

An oxygen sensor having a main body member with an interior chamber, made from material which is an oxygen ion conducting solid electrolyte when at specified temperatures. Electrodes made from material which is porous to oxygen molecules are positioned opposite each other on the main body member, within the interior chamber an d on the outside of the main body. Via a port which extends through the main body, changes in the absolute pressure of gas to be tested in the environs of the outer electrode are transmitted to the gas in the environs of the inner electrode. As a result of reference gas being introduced into the interior chamber of the main body through an orifice at a pressure sufficient to maintain the rate of flow at its critical (and therefore constant) rate of flow, the environs of the inner electrode are occupied by reference gas and a flow of gas results, through the main body member from the region of the inner electrode and out through the port.

In optional embodiments, only a portion of the test gas directly impinges upon the outer surface of the outer electrode to minimize it being cooled, the main body member is heated to specified temperatures, means are provided to ensure a flow of test gas past the sensor, and/or the outside electrode periodically is exposed to reference gas to calibrate the sensor for cell constant.

20 Claims, 3 Drawing Sheets

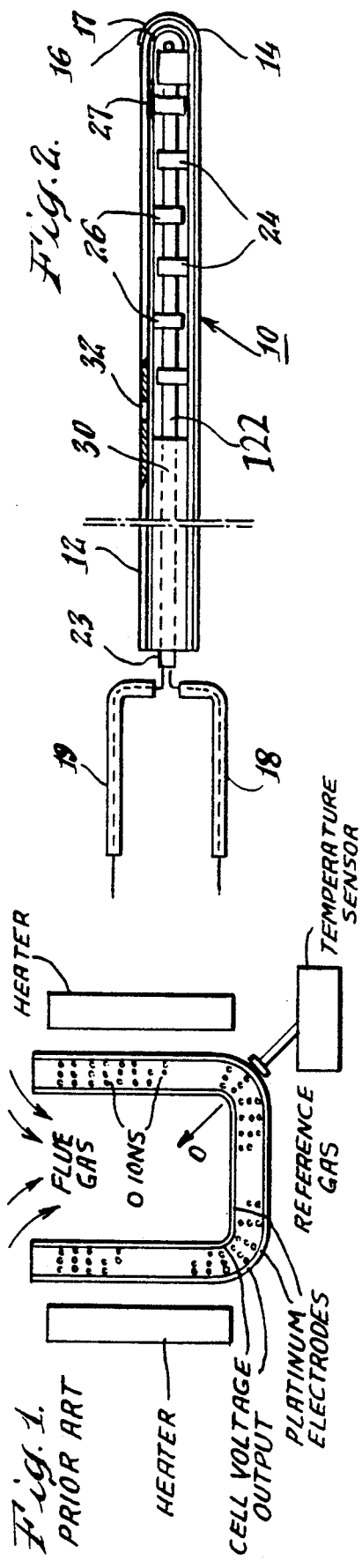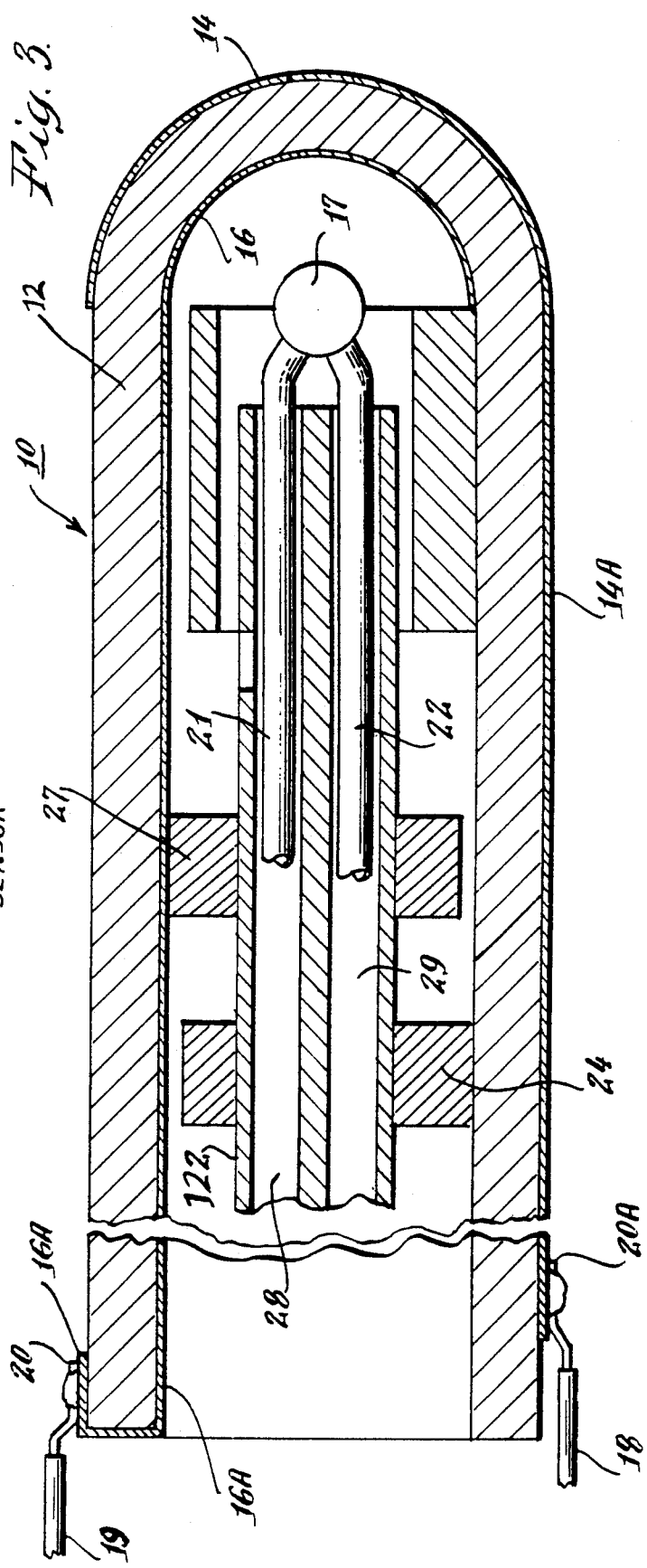

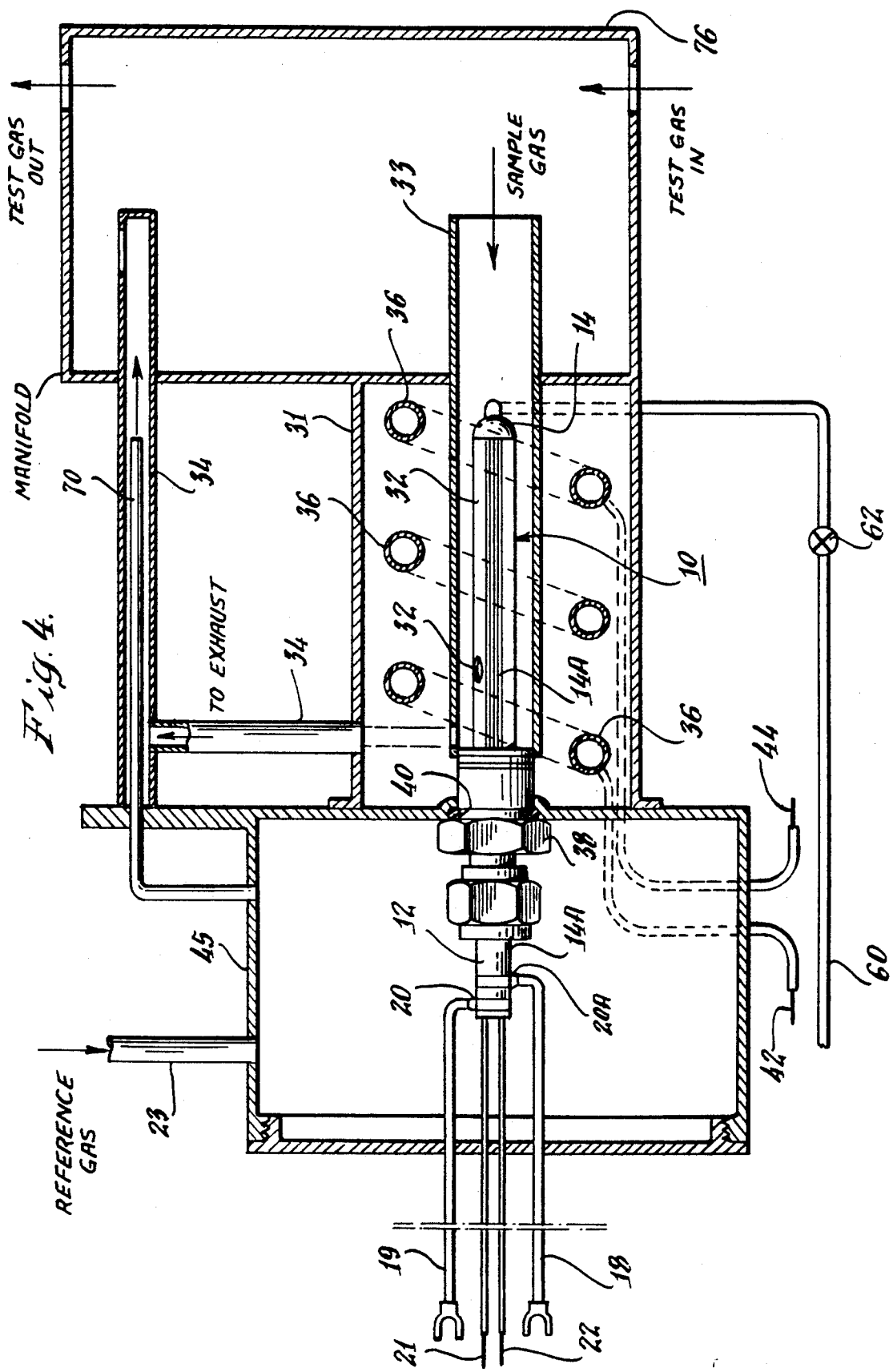

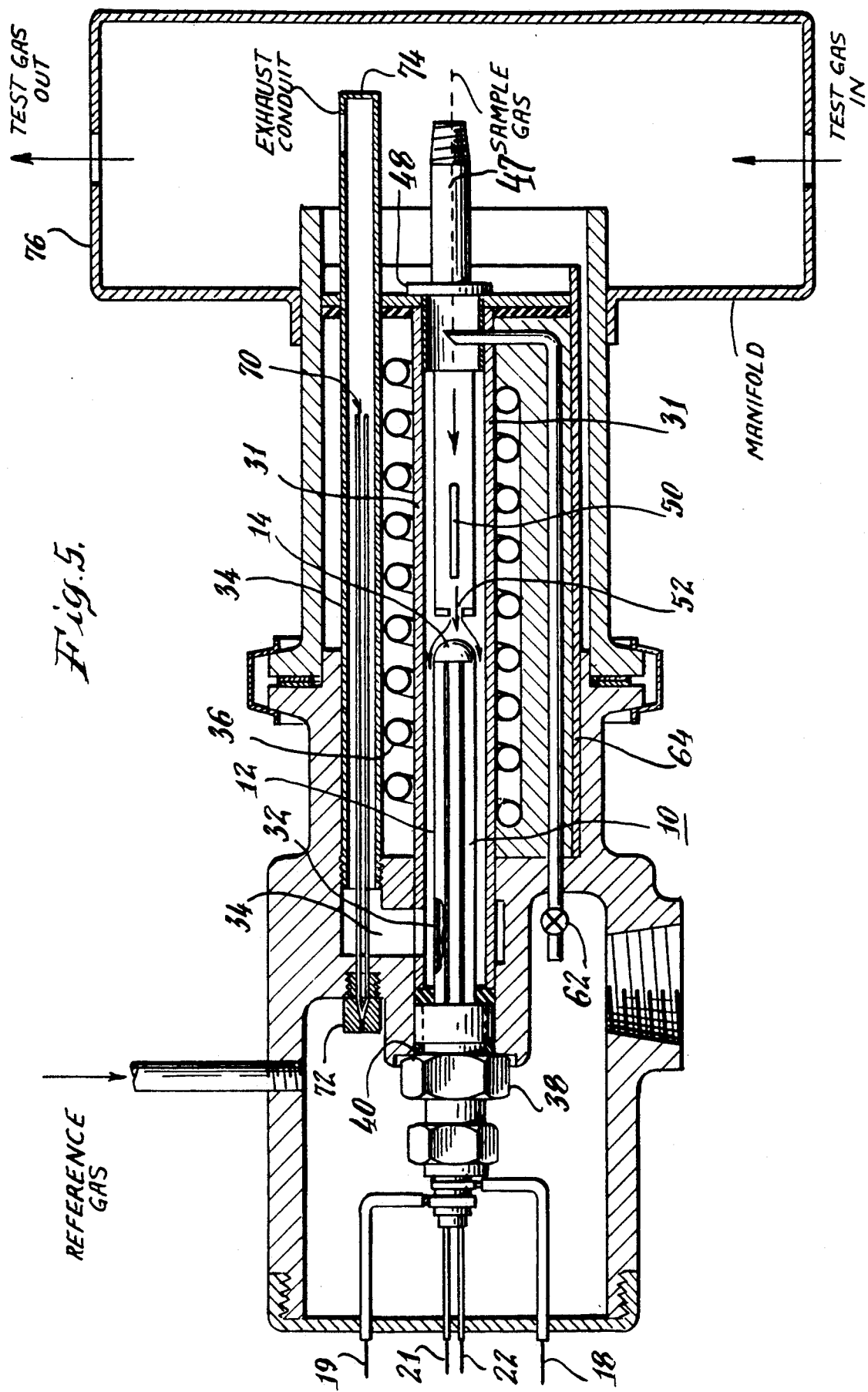

OXYGEN MONITORING DEVICES

BACKGROUND OF INVENTION

In certain applications, it is desired to monitor the oxygen content of gases more or less continuously. A system which does this effectively may be used, for example, to monitor the gaseous effluent from industrial boilers, kilns, ovens, internal combustion engines, driers, heat treating furnaces, incinerators, refinery process units, gas turbines scrubbers and the like. Based on the information so gleaned, the amount of oxygen present may be adjusted to desired levels. For example, the air being introduced into the combustion phase of a boiler may be regulated to achieve optimum efficiency, and to reduce nitrous oxide and/or sulphur dioxide emissions. Insufficient oxygen, which can cause too high smoke opacity, slag buildup, boiler tube fouling, decreased heat transfer, excessive maintenance, and wasted fuel, may be avoided, as also can an excess of oxygen which can cause waste of energy by heat loss. Such monitoring systems can also be adapted to act as sources to enable feedback systems to effectuate such adjustments automatically and continuously.

One means for so monitoring the oxygen content of such gases works on the principle of a zirconium oxide fuel cell oxygen sensor. Typically, such sensors consist of a ceramic tube made from zirconium oxide that has been stabilized with yytrium and has porous platinum electrodes coated opposite each other on both its inner and its outer surfaces at its sensing end. When the cell is heated to a temperature above 600° C. (1100° F.) the ceramic material becomes permeable to oxygen ions. Vacancies in its lattice structure permit such ions to pass through it, thus rendering the cell into an oxygen ion conducting solid electrolyte. When the number of oxygen molecules per unit volume is greater at one plate of the cell than at the other, oxygen ions will migrate from the former to the latter. The platinum electrodes on each side of the cell wall provide catalytic surfaces for the change of oxygen molecules into oxygen ions and vice versa. Thus, oxygen molecules entering the cell through an electrode gain electrons to become ions which enter the electrolyte. Simultaneously, at the other electrode, the oxygen ions lose electrons and are released from the surface of the electrode as oxygen molecules. This flow creates an electron imbalance which produces a voltage potential between the electrodes. The magnitude of that potential is a function of the temperature of the cell and the relative partial pressure on each side of the cell. Partial pressure is defined as the pressure exerted by each component in the mixture that goes to make up the gas. It may be calculated as follows:

$$Pi = Ni \times R \times T/V$$

where
pi = the partial pressure,
Ni = the number of molecules of the specie,
R = the Universal Gas constant,
T = temperature (absolute scale),
and V = volume.

The partial pressure of the component gas "i" is then the same as if it occupies the same volume at the same temperature in the absence of other gases.

The relationship between the oxygen partial pressure at the monitored side and that at the reference gas side (typically air, which is 20.95% oxygen by volume), the temperature, voltage output, and cell constant of the individual cell are defined by the "Nernst" equation as follows:

$$E = RT/4F \times Ln(P1/P2) + C$$

where E = Voltage out,
T = Absolute temperature of cell
R = Universal Gas Constant
F = Faraday's Constant
P1 = Partial Pressure of oxygen in the reference gas
P2 = Partial Pressure of oxygen in the monitored gas
C = a Cell Constant for each individual cell,
and Ln(P1/P2) is the natural logarithm of ratio P1/P2.

The electrical voltage output of such a cell may be utilized, for example, in a closed loop combustion control system which uses the oxygen sensor output signal to "trim" the fuel/air mixture ratio. In such systems, the readings for actual stack gas oxygen content are compared with a desired set point. An appropriate control system output is generated to adjust automatically the fuel/air ratio, by such means as changing the amount of combustion air to the burner and/or the amount of fuel admitted to the burner, adding diluents and/or oxygen, etc., thereby assuring that the desired oxygen set point is maintained. The desired effect of this is to achieve optimum combustion efficiency by regulating exactly the amount of oxygen to achieve complete combustion of the fuel. The Nernst equation "C" factor is to adjust output readings for peculiarities of the individual cell, such as those which may be induced by physical characteristics, damage, and/or conditions which are unique to that particular cell. Its value may be determined and utilized to correct the output readings by such means as a solenoid actuated bypass conduit through which reference gas may be periodically introduced to the environs of the outer electrode surface. The "reading" while that is being done will then be that of the "C" factor alone; all other factors affecting the cell output at that instant thereby having then been eliminated or at least so minimized as to have no material effect on the resulting readings.

It is also desired to effectuate such monitoring by comparable means and mechanisms to those previously described in situations where ambient phenomena may induce false output readings which render the cell ineffectual as a practical matter. One example of this is where there is a differential between the absolute pressure of the gas at one of the electrodes from that at the other. An even more difficult example is where such a differential in absolute pressure is pulsating. Thus, in an internal combustion diesel engine, the effluent gas not only is at an absolute pressure differential with respect to the reference, but also, because of the valving in the engine, that pressure pulsates through the exhaust system. Conditions of this type can cause a sensor of the type described to exhibit erroneous readings.

An explanation of this begins by noting that the principle involved in the operation of cells of the type described above is the migration of oxygen ions through the walls of the cell that is motivated by a disparity in the oxygen pressure as between the two masses of gas. To be an accurate indicator of the proportion of oxygen content in the test gas, this migration, and the resulting imbalance in electrical potential, should be solely the result of the differential between the partial pressure of the oxygen in the gas that is on the test side and that of the oxygen in the gas that is on the reference side of the cell. However, the magnitude of such migration may be influenced as well by a differential in the absolute pressure of the reference environment and that of the environment being sampled. The reason for this result is that the effect of an increase in absolute pressure is to compress the gas and thus "densify" it; i.e., to concentrate a greater number of oxygen molecules into an equivalent volume. But the sensor is capable only of reacting to oxygen pressure differentials. Its outer electrode now being exposed to more oxygen molecules over the same area for that electrode due to the "densification" which has occurred, the sensor "reads" this as if the composition of the test gas had changed through an increase in the proportion of its oxygen constituent, which it has not. To interpret the resulting output as indicative of an oxygen partial pressure differential reading therefore, is erroneous since it has not been factored to take this absolute pressure differential element into account. While theoretically it might be possible to factor the cell output to take such absolute pressure differentials into account, this would be an unrealistically complex approach as a practical matter. In a pulsating pressurized environment particularly, such as that present in an internal combustion engine exhaust system, not only is such an aberration produced by the addition in absolute pressure, but the aberration produced is unstable since the added pressure so applied is constantly changing due to the exhaust valve operation of the engine. It will be apparent then why, although the use of devices of the type described is desired, that has not been practical in some situations because of the inaccuracy of the results produced.

Accordingly, it is an object of this invention to provide means to detect the oxygen content of a gaseous environment.

Another object of this invention is to provide such means for use in monitoring such oxygen content on a more or less continuous basis.

Yet another object of this invention is to provide means for achieving one or more of the foregoing objectives that is adapted for use in contexts wherein such gaseous environments are at differing absolute pressures.

Still another object of this invention is to provide means for achieving one or more of the foregoing objectives that is adapted for use in contexts wherein such gaseous environments are pulsating.

Yet another object of this invention is to provide means for achieving one or more of the foregoing objectives that is adapted for producing repetitive output signals to be utilized as corrective feedback sources.

Another object of this invention is to provide means for achieving one or more of the foregoing objectives that is adapted for use in internal combustion engines.

STATEMENT OF INVENTION

Desired objectives may be achieved through practice of this invention, embodiments of which include a oxygen sensor that has a main body member that is made from material which is an oxygen ion conducting solid electrolyte when at specified temperatures and has an internal cavity, electrodes that are porous to oxygen molecules juxtaposed to said main body member in its internal cavity and on its outside surface and opposite each other, means for transmitting the absolute pressure of gas at said outer electrode to gas at said inner electrode, and means for supplying reference gas to the environs of said inner electrode through an orifice at pressure sufficient to maintain its critical flow rate.

Optionally, embodiments may include (1) means by which only a selected portion of said stream of gas impinges directly upon said outer electrode; (2) means for heating said main body member to such specified temperatures; (3) means for periodically calibrating the sensor for its "C" factor; (4) means to ensure that the environs of said outer electrode are occupied by gas to be tested; (5) means for isolating the environs of said inner electrode from infiltration by gas being tested via said pressure change transmitting means; and/or (6) means to ensure that there is a positive flow of gas outward from said internal cavity.

DESCRIPTION OF DRAWINGS

This invention may be understood from the description which follows and from the accompanying drawings in which FIG. 1 is a cross-sectional view of a prior art fuel cell oxygen sensor, FIG. 2 is a cross-sectional view of an embodiment of this invention, FIG. 3 is a cross-sectional view of a detailed portion of the embodiment of this invention shown in FIG. 2, and FIG. 4 is another cross-sectional view of the embodiment of this invention shown in FIGS. 2 and 3, and FIG. 5 is a cross-sectional view of another embodiment of this invention.

DESCRIPTION OF PREFERRED EMBODIMENTS

In FIG. 1 there is depicted a cross-sectional view of a prior art fuel cell oxygen sensor. It includes a central main body in the form of a ceramic tube made from yytrium stabilized zirconium oxide, with porous platinum electrodes coated on its inner and its outer surfaces. When the cell is heated, as by the heaters which surround it, to a temperature above 600° C. (1100° F.) it becomes permeable to oxygen ions. Vacancies in its lattice structure permit such ions to pass through it, thus rendering the cell into an oxygen ion conducting solid electrolyte. The platinum electrodes on each side of the cell provide the catalytic surfaces for the change of oxygen molecules into oxygen ions and vice versa. Oxygen molecules on the (outer) reference gas side of the cell, where the number of oxygen molecules is higher per unit volume, gain electrons and become ions when they are caused by the higher partial pressure on that side of the cell to pass through the outer, porous platinum coating and to enter the electrolyte. When such ions pass through the inner electrode, they are caused to lose electrons, rendering them back into oxygen molecules that are then released from the surface of the inner electrode. Thus, whenever the partial pressure of oxygen is different at one side of the cell compared to that at the other, as when one side is exposed to flue gases while the other is exposed to normal atmosphere, oxygen ions will migrate from the higher partial pressure side to the lower oxygen pressure side. The electron additions and deletions which take place as the oxygen passes through each of the platinum coatings generate a net imbalance of electrons as between the two electrodes, and that produces a voltage potential between them. The magnitude of that potential is a function (among other things) of the oxygen partial pressures on each side of the cell. By eliminating or compensating for those other factors, the oxygen density per unit volume on the test sample side may thereby be detected. The relationship between the partial pressure of the oxygen in the monitored gas and the reference gas (typically air, which is 20.95% oxygen by volume), and the temperature, voltage output, and cell constant of the individual cell are defined by the "Nernst" equation, as previously noted.

This detection approach is basically a partial pressure differential phenomenon. However, as has also been previously noted, phenomena which can affect the electrical potential so generated may not be restricted to differentials in partial pressure. Therefore, such prior art devices cannot measure accurately the oxygen content of gas in a test zone when it is at an absolute pressure different from that of the gas in the reference zone. This deficiency is even more unsatisfactory where, as with internal combustion engine exhaust systems, the absolute pressure in the test zone is constantly pulsing or otherwise changing with fair rapidity.

FIG. 2 illustrates, in cross-section, an embodiment of this invention in the form of a sensor 10 which overcomes these shortcomings. As such, it includes a ceramic main body member 12 made from yytrium stabilized zirconium oxide, with porous platinum electrodes 14, 16 coated on the inside and outside respectively of the sensing end of the sensor. These electrodes 14, 16, have strip-like extensions 14A and 16A respectively, which extend along the length of the outside and inside respectively of the main body member 12, as a means to conduct the electrical output of the electrodes to a point where it can be picked up outside the sensor itself. This is shown in FIG. 3. There, in a cross-section of the sensor end of the sensor device shown in FIG. 2, the inner electrode 16 is shown to have a continuation ribbon 16A which extends from that electrode along the inside of the length of the main body 12 to its opposite end, where it extends across the end of the wall of the main body 12 and doubles back for a short distance. Through a soldered connection 20, its output is carried off via an insulated conductor 19. Similarly, a ribbon of platinum 14A conducts the output of the inner electrode 14 along the outside of the length of the main body to a connector 20A, through which its electrical output is conducted via another soldered connection 20A to another insulated electrical conductor 18. The shape of the body member in this embodiment is like that of a test tube, in that it is closed at the sensing end of the sensor where the electrodes are located, and has a central chamber. Other structures, however, may also be utilized, such as square, rectangular, or other shaped boxes with internal cavities adapted for particular uses. As shown in FIGS. 2, 4, and 5, the main body member 12 has a port or bleed hole 32 which extends through its sidewall, by means of which absolute pressures at the outside of the main body will be transmitted its internal cavity. The sensor also includes a central tube 122 which has two internal conduits 28, 29 which extend the length of the interior chamber. These conduits open to the reference gas source at the non-sensing end of the tube, and open into the region of the inside electrode 16 within the main body member 12 at its closed end. By means of these conduits, reference gas may be introduced directly to the environs of the inner electrode as will be described. Surrounding the central tube 122, at spaced intervals along its length, are spacers 24, 26 made from ceramic material of the type as is the main body 12. It should be noted that those spacers marked "24" have a space between their tops and the inside of the main body 12, while those marked "24" have comparable spaces at their bottoms. These may be formed by chording what are otherwise circular spacers, alternating top and bottom. The effect of this alternating gap pattern is to create tortuous paths which tend to dampen or attenuate the flow of gas linearly through the body member 12 and, more importantly, serve to increase the length of the travel path which gas would have to travel from the port 32 to the environs of the inner electrode 16. The significance of this latter, in particular, will be elaborated upon later, from which it will be apparent that desired results may be achieved with other forms of such isolation means (e.g., fibrous "wool") in addition or in the alternative. A plug 30 or other means seals the open end of the main body member 12 while allowing the various electrical leads to be brought out to the outside of the main body 12. Included among them are electrical conductor leads 21, 22 which conduct the output of a thermocouple 17. By this means, the temperature of the sensor may be monitored to facilitate maintaining it above the 600° C. level necessary for the ceramic component of the wall of the main body 12 to function as a solid electrolyte as previously described.

FIG. 4 illustrates in cross-section the embodiment of this invention shown in FIGS. 2 and 3 with other components with which it may be used. These added components include an outer housing 31, a sample gas inlet 33, and an exit tube 34 which extends from the compartment surrounding the sensor 10. These several components are held in place and sealed by means of known per se means, such as the retention nut 38 and the 0 ring seal 40. The heating coil 36 is supplied with electrical energy by means of the power leads 42, 44 as a means to maintain the unit at a desired 600°+C. temperature level. There is also an outer box 45 with a screw-on cover for access which is, nevertheless, gas tight so that reference gas admitted to it via the gas inlet 23 may be caused to flow into the open ends of the conduits 28, 29 and along their length into the environs of the inner electrode 16 as herein described.

The apparatus shown in FIG. 5 as well as that shown in FIG. 4 also includes a reference gas conduit 60 through which reference gas may flow periodically according to a predetermined program as regulated by a solenoid valve 62, for example, into the environs of the outside electrode 14. By this means, the sensor device may periodically be "zeroed" as to all affecting factors except for the "C" factor of individual cell variations according to the Nernst formula. This effect is achieved because when both electrodes in the sensor are exposed to gas of the same oxygen composition and the same absolute pressure, any read-out that occurs will be a reflection of any aberration that is peculiar to that cell and its environment, and so may be used to compensated test readings for those peculiarities. In both cases, the calibration gas solenoid 62 receives its gas supply directly from the pressurized reference gas plenum, and the flow of calibration gas to the sensing cell is controlled by an appropriately sized orifice built directly into the solenoid body.

In the embodiment shown in FIG. 4, reference gas from the end housing flows at a controlled rate into an aspirator tube 72 that is positioned more or less coaxial to and within the exhaust tube 74. The latter terminates in a nozzle 74 which vents this exhaust in the direction of flow of the test gas as it passes through the manifold 76. A similar, but alternative structure is shown in FIG. 5, with corresponding elements identified by the same reference numerals. While other structures may be used to achieve comparable ends, these embodiments are illustrative of eductors which may be used as a means to ensure a positive flow of gas outward from the interior chamber of the sensor device. The high pressure reference gas supply furnishes the motive power for the aspirator. The exhaust conduit and the test gas inlet are located in close proximity to each other to ensure that the two tubes are at substantially the same absolute pressure where they are open to the mass of gas being sampled. The exhaust tube is located downstream of the test gas inlet to eliminate pollution of the test gas inlet by the exhaust flow. The aspirator flow control orifice limits the flow to the aspirator so that a sufficient test gas flow rate is maintained. The negative pressure created by the aspirator is a driving force that causes a sample of test gas to be drawn into the test gas inlet, past the sensor and out through the exhaust conduit 34, and also carries away gas exiting the sensor main body via the port 32. Thus, during testing, the outer electrode "sees" test gas that is representative of the mass of gas being tested, and the inner electrode "sees" reference gas.

The eductor assembly and the reference gas conduits preferably are located in the heated areas of the sensor since this eliminates condensation and minimizes temperature "excursions" at the sensing cell.

From these Figures, the operation of this embodiment of this invention may be seen. When the complete assembly is installed in place for use, sample gas (i.e., that gas whose oxygen content is to be ascertained), such as exhaust gas from a diesel engine, is admitted through the sample gas inlet 33, so that it impinges upon and occupies the environs of the outer electrode 14 of the sensor 10. Sample gas so admitted to the unit passes along the length of the outside of the outer main body 12. As a result, any differential in absolute pressure between that of the body of sample gas being tested and that of the reference gas which is inside the device and in the environs of the inner electrode 16 is transmitted via the hole 32 to the inside of the main body member 12. The effect of this effectively is to nullify any differential between the absolute pressures of the two bodies of gas other than the differential in partial pressure between them which, of course, are what is desired to be detected.

It should be noted that this result occurs as to any differential in absolute pressure between the two regions, which may be more or less constant, or it may pulsate as does the exhaust from a diesel or other internal combustion engine. Further, the pressure in the test or sample zone may be negative compared to that in the reference zone, and likewise may be constant or pulsate compared to that of the reference zone. As will presently be seen, embodiments of this invention may be made to operate in all such situations.

These results are assured by the manner in which the reference gas is introduced into the environs of the inside electrode 16 via the ducts 28, 29 in the inner tube 122. According to well known principles of physics, the general rule is that the flow rate of gas through an orifice is a function of the difference in pressure between the two sides of the orifice. However, when the ratio of pressure on the "out" side is about 53% of that on its "in" side, the critical flow rate for that orifice is reached. At that point, the rate of flow will stabilize and will not increase or decrease so long as the ratio of "out" to "in" pressures is maintained at or above that 53+% level. The flow of gas from these ducts is maintained at the level of critical flow for the orifices through which it flows. As a result, the volume of reference gas entering the internal cavity of the main body will not decrease or increase, even when changes occur in the absolute pressure of the gas being tested. To that end, the pressure at the "in" side of the inlet orifices is maintained at a level such that a pressure equal to 53% of that level (i.e., the pressure at the "out" side of that same orifice) is at least slightly greater than the actual constant pressure or the peak of the pulsating pressure (as the case may be) of the sample gas. This maintains a net outflow of the reference gas from the exposed surface of the inner electrode 16 inside the main body 12 out through the port 32, from whence it can move along to and out through the exhaust tube 34. This result is enhanced by the previously described isolation means which, in addition to the dampening or attenuation functions, lengthens the travel path for this outflow of reference gas. As a result, any invasion of test gas into the inner cavity via the port 32 due to a transient excess of test gas absolute pressure over that of the reference gas, and contamination of the reference gas in the environs of the inner electrode, is precluded. Correspondingly, if the absolute pressure, constant or pulsating, of the test gas is negative (i.e., is a partial vacuum) with respect to that of the reference gas, the net outflow will remain substantially constant due to the throttling effect inherent in the constancy of the critical flow phenomenon at the reference gas injection orifices. Since this also ensures a net outflow of reference gas from the interior of the sensor, it is assured that the environs of the inner electrode 16 will always be occupied by reference gas, uncontaminated by sample gas leaking through the port 32 into the interior of the main body member 12, thus preserving the basis upon which accurate readings of partial pressure differentials (and therefore of oxygen content) may be premised.

Some consideration must be given to the hole sizes of the inlet and outlet orifices, since this may have an effect on the accuracy of the readings obtained. Thus, the inlet orifice must be sufficiently large to introduce a volume of gas that will assure a positive net outflow from the inner chamber while, at the same time, not being so large as to permit so much gas to enter the chamber that it will have a cooling effect on the device or otherwise affect its output. Such adjustment are within the capability of one skilled in these arts once given these teachings of this invention. It should also be noted that the outlet orifice ordinarily should be somewhat larger in size than the inlet orifice to ensure that it relieves quickly any pressure built up in the inner chamber. It is recognized, too, that some pressure drop normally will be exhibited across the outlet orifice which may effect the accuracy of the device. However, the effect of this, if any, is taken into account when a reading is taken as previously described to calibrate the device for its "C" factor. In effect, this element becomes part of the read cell factor.

Sometimes, again as in the case of an internal combustion diesel engine, the pulses in the sample (exhaust) zone are so frequent in time duration and of such a magnitude that the sample gas impinging upon the outer electrode 14 does so at high velocities and volumes and so can produce false readings. To ameliorate this, the embodiment of this invention shown in FIG. 5 may be used. It includes a sensor 10 within a heated housing 31. However, instead of the sample gas coming at the sensor through a sample gas inlet of the type shown as 33 in FIG. 4, a sample gas inlet tube 47 is positioned within the sample gas inlet and sealed with respect to it by means of a seal ring nipple 48, so that the sample gas admitted to the unit comes entirely through the tube 47. The tube 47 is made so that it has a small tap hole 52 at its end that is juxtaposed to the electrode 14, and has comparatively large cross-sectional area holes 50 in the sides of the inlet tube 47 but within the sealed off region. By this means, only a small portion of the total incoming test gas, which nevertheless compositionally is statistically representative of the test gas but of small volume and low velocity, actually impinges upon the electrode 14, thus eliminating or at least minimizing any readout aberrations that would otherwise be volume and/or velocity induced. At the same time, the unit still has large volume test sample capability by virtue of the side holes 50 which permit most of the sample gas to bypass the electrode 14 but to pass through the test apparatus anyway. Such large volume capacity for the unit as a whole may be necessary in order to ensure, particularly with a pulsating source, that the sample tested is representative, and not merely the re-injection of a previously monitored or otherwise unrepresentative sample.

It should be noted that the calibration air circuit which includes the conduit 62 and the solenoid 60 of the embodiment as shown in FIG. 5, while otherwise comparable in design and function with that shown in FIG. 4, discharges into the tube 47 in the region of the nipple 48, well ahead of the lateral tube slots 50. This discharge position is selected to provide sufficient time for the calibration gas, as it travels along the tube in the direction of the sensor electrode 14, to heat sufficiently for it not to introduce any temperature induced errors in the sensor readings. However, given the distance involved in assuring that result, consideration must be given to ensuring that a sufficient volume of calibration gas is introduced so that the calibration gas which the sensor electrode 14 "sees" is substantially undiluted with test gas and is truly representative of the composition of the calibration gas. Such concepts are not limited to embodiments of the type shown in FIG. 5, but are applicable to other embodiments of this invention as well. Such adjustments are within the skills of persons knowledgeable in the cognizant arts.

FIGS. 4 and 5 also illustrate means for heating the entire sensor unit in the form of a heating coil 36 that is energized by electrical energy through conductor leads 42, 44. Normally, given the high temperature (600+° C.) that must be established and maintained in order for zirconium oxide to become oxygen ion conductive, such supplementary heating means is required in the current state of this technology. However, it is within the contemplation of this invention that technological advances may be made such that the necessity for such supplementary heating is reduced or negated.

From the preceding description and the accompanying drawings, it will be clear that many different embodiments and variants thereof may be employed within the contemplation of this invention. For example, although single pressure relief ports and pairs of electrodes have been described and discussed in the embodiments, it is within the contemplation of this invention that multiple ports and/or combinations of electrodes may be used within recognized engineering considerations and practices. Thus, it is to be understood that the embodiments illustrated and discussed are by way of illustration and not of limitation, and that a wide variety of embodiments may be made without departing from the spirit or scope of this invention.

We claim:

1. An oxygen sensor comprising
an elongated main body member which is made from yytrium stabilized zirconium oxide and has an internal chamber at one end,
two electrodes that are made from platinum and are in contact with said main body, one of which is an inner electrode positioned within said chamber at one end of said main body, and the other of which is an outer electrode positioned on the outside surface of said main body member substantially opposite said inner electrode,
electrical conductor means by which said electrodes are rendered electrically accessible from the other end of said main body,
an opening into said chamber from the outside of said main body via which the absolute pressure of gas in the environs of said outer electrode is transmitted to gas in the environs of said inner electrode,
isolation means for isolating the environs of said inner electrode from infiltration by gas being tested via said openings, and
supply means including an orifice for supplying reference gas to the environs of said inner electrode at a pressure to cause it to flow at its critical flow rate through said orifice.

2. The device described in claim 1 including calibration means for periodically introducing reference gas to the region of said outside electrode.

3. The device described in claim 1 including heating means for heating said main body member to a temperature of at least 600 degrees centigrade.

4. The device described in claim 2 including heating means for heating said main body member to a temperature of at least 600 degrees centigrade.

5. The device described in claim 3 including monitoring means that is adapted for monitoring the temperature of said main body and is also adapted for being monitored by regulating means to maintain the temperature of said main body at at least 600 degrees centigrade.

6. The device described in claim 4 including monitoring means that is adapted for monitoring the temperature of said main body and is also adapted for being monitored by regulating means to maintain the temperature of said main body at at least 600 degrees centigrade.

7. The device described in claim 1 including control means for directing a selected portion of the gas to be tested to occupy the environs of the outer surface of said outer electrode.

8. The device described in claim 2 including control means for directing a selected portion of the gas to be tested to occupy the environs of the outer surface of said outer electrode.

9. The device described in claim 3 including control means for directing a selected portion of the gas to be tested to occupy the environs of the outer surface of said outer electrode.

10. The device described in claim 4 including control means for directing a selected portion of the gas to be tested to occupy the environs of the outer surface of said outer electrode.

11. The device described in claim 5 including control means for directing a selected portion of the gas to be tested to occupy the environs of the outer surface of said outer electrode.

12. The device described in claim 6 including control means for directing a selected portion of the gas to be tested to occupy the environs of the outer surface of said outer electrode.

13. An oxygen sensor comprising
a main body member which has an interior chamber and is made from material which is an oxygen ion conducting solid electrolyte when within a specified temperature range,
at least two electrodes that are porous to oxygen molecules, at least one of which is an inner electrode positioned on a wall of said interior chamber and at least one other of which is an outer electrode positioned on the outside surface of said main body member substantially opposite said inside electrode,
electrical conductor means by which said electrodes are rendered electrically accessible at the outside of said main body,
at least one opening into said interior chamber from the outside of said main body via which the absolute pressure of gas in the environs of said outer electrode is transmitted to gas in the environs of said inner electrode,
isolation means for isolating the environs of said inner electrode from infiltration by gas being tested via said openings, and
supply means including an orifice for supplying reference gas to the environs of said inner electrode at a pressure to cause it to flow at its critical flow rate through said orifice.

14. The device described in claim 13 including at least one from among the group consisting of calibration means for periodically introducing reference gas to the region of said outside electrode, heating means for heating said main body member to such specified temperature range, monitoring means that is adapted for monitoring the temperature of said main body and is also adapted for being monitored by regulating means to maintain the temperature of said main body at said specified temperature range, impeller means adapted to cause test gas to flow past the exterior of said main body, and control means for directing a selected portion of the gas to be tested to occupy the environs of the outer surface of said outer electrode.

15. A method of detecting the proportion of oxygen as a constituent part of a mass of gas using an oxygen sensor comprising a main body member which has an interior chamber and is made from material which is an oxygen ion conducting solid electrolyte when within a specified temperature range; at least two electrodes that are porous to oxygen molecules, at least one of which is an inner electrode positioned on a wall of said interior chamber and at least one other of which is an outer electrode positioned on the outside surface of said main body member substantially opposite said inside electrode; electrical conductor means by which said electrodes are rendered electrically accessible at the outside of said main body; at least one opening into said interior chamber from the outside of said main body via which the absolute pressure of gas in the environs of said outer electrode is transmitted to gas in the environs of said inner electrode; isolation means for isolating the environs of said inner electrode form infiltration by gas being tested via said openings; and supply means including an orifice for supplying reference gas to the environs of said inner electrode at a pressure to cause it to flow at its critical flow rate through said orifice; comprising the steps of
establishing the temperature of said main body to within said specified temperature range,
causing the environs of said outside electrode to be occupied by gas to be tested,
supplying reference gas to the environs of said inner electrode at a pressure to cause it to flow at its critical flow rate through said orifice and
detecting the electrical output of said electrodes and translating said output into a value for the oxygen composition of said gas being tested.

16. The method described in claim 15 wherein said step of establishing said temperature of said main body includes utilizing supplementary heating means.

17. The method described in claim 15 including the added steps of
periodically introducing reference gas into the environs of said outside electrode while monitoring the electrical output of said electrodes to determine the "C" factor of said cell, and
calibrating the electrical output of said sensor for said "C" factor.

18. The method described in claim 16 including the added steps of
periodically introducing reference gas into the environs of said outside electrode while monitoring the electrical output of said electrodes to determine the "C" factor of said cell, and
calibrating the electrical output of said sensor for said "C" factor.

19. The method described in claim 17 including the added steps of
utilizing said electrical output of said electrodes as a drive signal to adjust automatically the oxygen constituent of said gas being monitored.

20. The method described in claim 18 including the added steps of
utilizing said electrical output of said electrodes as a drive signal to adjust automatically the oxygen constituent of said gas being monitored.

* * * * *